United States Patent [19]

Buntin

[11] 4,102,673
[45] Jul. 25, 1978

[54] 1-PHENYL-HEXYL UREAS AS HERBICIDES

[75] Inventor: George A. Buntin, New Castle, Del.

[73] Assignee: Hercules Incorporated, Wilmington, Del.

[21] Appl. No.: 336,600

[22] Filed: Feb. 28, 1973

Related U.S. Application Data

[63] Continuation-in-part of Ser. No. 155,340, Jun. 21, 1971, abandoned, which is a continuation-in-part of Ser. No. 756,424, Aug. 30, 1968, abandoned.

[51] Int. Cl.$^2$ .................. A01N 9/20; C07C 127/15; C07C 127/19
[52] U.S. Cl. .................. 71/120; 260/553 A
[58] Field of Search .................. 71/120

[56] References Cited
U.S. PATENT DOCUMENTS

| 2,655,447 | 10/1953 | Todd | 71/120 |
| 2,655,534 | 10/1953 | Searle | 71/120 X |
| 2,728,654 | 12/1955 | Gerjovich | 71/120 |
| 2,781,330 | 2/1957 | Downey | 260/45.9 |
| 3,277,061 | 10/1966 | Fenton | 71/120 |

OTHER PUBLICATIONS

Mailhe, C. R., 172, 693, Bl (4) 29, 222 [Beilstein Bond XII, Syst. No. 1627, Zweites Ergonzungswerk.].
Turner, et al., J. Chem. Soc., (Nov. 1965) p. 6435.

Primary Examiner—Catherine L. Mills
Attorney, Agent, or Firm—George H. Hopkins

[57] ABSTRACT

Disclosed is the herbicidal use of compounds of the formula:

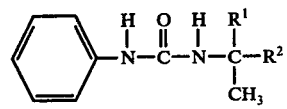

in which $R^1$ is H or $CH_3$, and, when $R^1$ is H, $R^2$ is selected from the group consisting of $CH_2-CH_2-CH_2-CH_3$,

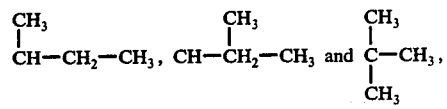

and, when $R^1$ is $CH_3$, $R^2$ is selected from the group consisting of $CH_2-CH_2-CH_3$ and

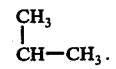

Compounds of the formula in which, when $R^1$ is H, $R^2$ is selected from the group consisting of $CH_2-CH_2-CH_2-CH_3$,

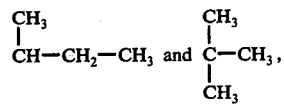

and, when $R^1$ is $CH_3$, $R^2$ is $CH_2-CH_2-CH_3$, are new.

12 Claims, No Drawings

1-PHENYL-HEXYL UREAS AS HERBICIDES

The application is a continuation-in-part of the co-pending U.S. patent application Ser. No. 155,340, filed June 21, 1971, now abandoned which in turn is a continuation-in-part of the then copending U.S. patent application Ser. No. 756,424, filed Aug. 30, 1968, now abandoned.

This invention relates to N-aryl ureas and to herbicidal compositions and processes involving them.

This invention is based upon the discovery that certain 1-phenyl-3-($C_6$ alkyl)ureas, some of which are new, have selective phytotoxicity. At concentrations at which they are tolerated by a number of crop plants, they kill weeds.

In summary, this invention comprises the herbicidal use of compounds represented by the structural formula I:

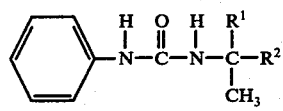

in which $R^1$ is H or $CH_3$, and, when $R^1$ is H, $R^2$ is selected from the group consisting of $CH_2$—$CH_2$—$CH_2$—$CH_3$,

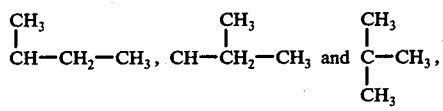

and, when $R^1$ is $CH_3$, $R^2$ is selected from the group consisting of $CH_2$—$CH_2$—$CH_3$ and

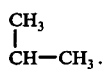

The compounds covered by structural formula I, which are old, and references disclosing them are as follows:

| Name | Reference |
|---|---|
| 1-Phenyl-3-(1,3-dimethylbutyl)urea | Mailhe, C.r. 172, 693; Bl[4]29, 222 [Beilstein Band XII - Syst. No. 1627 - Zweites Erganzungswerk] |
| 1-Phenyl-3-(2,3-dimethyl-2-butyl)urea | Turner et al., J. Chem. Soc. (Nov. 1965), p. 6435. |

The compounds covered by formula I, which appear to be new, are crystalline solids at 20°-25° C. These compounds and their melting points are:

| Name | Melting Point (° C.) |
|---|---|
| 1-Phenyl-3-(3,3-dimethyl-2-butyl)urea | 177-179 |
| 1-Phenyl-3-(2-hexyl)urea | 115-116 |
| 1-Phenyl-3-(α,α-dimethylbutyl)urea | 110-112 |
| 1-Phenyl-3-(1,2-dimethylbutyl)urea | 98-99 |

These novel compounds are made by the reaction of phenyl isocyanate and the appropriate hexyl amine. The preparation of other 1-phenyl-3-alkyl ureas by reacting phenyl isocyanates and alkyl amines is well known (see, for instance, the U.S. Pat., No. 2,655,444, to Todd). The reaction conditions employed in such preparation in general are applicable in the synthesis of the novel compounds of this invention by the above reaction.

To use the compounds of structural formula I to kill weeds, the compounds preferably are incorporated into dispersible compositions. Such a composition comprises an effective quantity of phytotoxic material, and application aid material.

The phytotoxic material consists essentially of at least one compound of structural formula I. In some embodiments of this composition the phytotoxic material comprises only one compound of the formula. In other embodiments, the phytotoxic material comprises two or more compounds of the formula. In still other embodiments, it comprises one or more different substances having phytotoxic activity.

Specific embodiments of the dispersible composition of this invention range from concentrates of the phytotoxic material to the ultimate use composition that is applied in the field. Accordingly, an effective concentration of the phytotoxic material in the composition of this invention is in a broad range, generally being from about 0.1 to about 90% by weight of the composition. Higher and lower concentrations, however, are within the broader concepts of this invention. In concentrate embodiments, the concentration of the phytotoxic material generally is in a range from about 10 to about 90% by weight of the composition and preferably in a range from about 10 to about 50% by weight of the composition. In the ultimate use embodiments, the concentration generally is in a range from about 0.1 to about 20% by weight of the composition and preferably in a range from about 0.5 to about 10% by weight of the composition.

Application aid material is generally inert material that facilitates distribution or dispersion of the phytotoxic material when it is applied to soil or to foliage of undesirable plants. It encompasses diluents, carriers, extenders, surfactants, spreading agents, sticking agents, wind drift control agents, and the like.

In those embodiments of the composition of this invention, which are normally solid, the application aid material generally comprises an inert solid in a divided condition.

Some embodiments of the solid composition are granular, while others are dispersible powders or dusts.

The granular compositions are of the coated type, the impregnated type or the incorporated type.

The coated type of granular composition is made by dusting a wettable powder or ground powder comprising the phytotoxic material onto inert granular carrier material which either before or after the dusting has been admixed with an inert adhesive or a sticker. Water, oils, alcohols, glycols, aqueous gums, waxes and the like including mixtures thereof, are used as stickers. Examples of inert granular carrier material include attaclay, corn cobs, vermiculite, walnut hulls and almost any granular mineral or organic material screened to the desired particle size (generally 15-60 mesh, preferably about 30 mesh, U.S. screen size). Generally the phytotoxic material is about 2-20% by weight of the composition, the sticker is generally about 5-40% by weight of the composition, and the granular carrier material is generally about 60-93% by weight of the composition.

In the case of the impregnated type of granular composition, the phytotoxic material as such when liquid or after melting, or dissolved in a solvent, is sprayed on or poured into the inert granular carrier material. The solvent can be removed by evaporation, or permitted to remain. In either case, the phytotoxic material impregnates the particles of the granular carrier material. Examples of the inert granular carrier material include those just mentioned with respect to the coated type of granular composition. The phytotoxic material is generally about 2-20% by weight of the composition, while the granular carrier material is generally about 80-98% by weight of the composition.

The incorporated type of granular composition is made by admixing the phytotoxic material with an inert finely divided solid such as, for example, clay, carbon, plaster of paris and the like, and made into a mud with water or other inert evaporable liquid. The mud is then dried to a solid sheet or cake, broken up or comminuted, and screened to the desired particle size (generally 15-60 mesh, preferably about 30 mesh, U.S. screen size). In other embodiments, the mud is put into a granulating pan and granules are formed therein with subsequent removal of the water or solvent. In still another procedure, the mud is extruded through a die into rods which are cut into small pieces. In the incorporated type of granular composition, the phytotoxic material generally is about 2-50% by weight of the composition, and the solid carrier material is about 50-98% by weight of the composition.

In all granular embodiments of the composition of this invention, various additives in minor concentrations relative to the carrier material also can be present.

In other embodiments of the solid composition of this invention, the carrier is usually a dispersible inert solid. A typical dispersible solid of this type is clay. Other suitable solids (dispersible solid) include talc, attapulgite, pyropylite, diatomaceous earth, kaolin, aluminum magnesium silicate, montmorillonite, fullers earth, sawdust and the like. The solid dispersible composition can be air dispersable, in which case it is usually referred to as a dust. Generally, when it is intended that the composition be water dispersible, the composition preferably contains emulsifying material (one or more surfactants) at a concentration sufficient to enable a suspension of the desired degree of stability to be formed when the composition is admixed with a suitable quantity of water. The composition in such case is usually referred to as a wettable powder. A typical dispersible solid composition of this invention generally comprises about 10-80% by weight of phytotoxic material, about 20-90% by weight of solid carrier material and, when emulsifying material is present, about 1-10% by weight of emulsifying material.

Other specific embodiments of the herbicidal composition of this invention comprise homogeneous liquid solutions of phytotoxic material in inert, preferably volatile, usually water-immiscible solvents for the phytotoxic material. Examples of suitable solvents include isophorone, cyclohexanone, methyl isobutyl ketone, xylene, and the like. Such a solution, which can be regarded as a concentrate, typically comprises about 10-50% by weight of phytotoxic material and about 50-90% by weight of solvent. The solution can be applied as is, or diluted with more solvent, or dispersed in water, or water dispersed in it. Preferably, when it is intended that the solution be dispersed in water or water dispersed in it, the mixture of solution and water also comprises emulsifying material at a concentration sufficient to enable a dispersion of the desired degree of stability to be formed when the solution or concentrate is mixed with water. A typical emulsifying material concentration is about 1-10% by weight of the concentrate. The water concentration generally is such that the phytotoxic material concentration preferably is about 0.5-10% by weight of the total composition.

Examples of the surfactants employed in both the liquid and solid compositions of this invention comprise the well-known surface active agents of the anionic, cationic and non-ionic types and include alkali metal (sodium or potassium) oleates and similar soaps, amine salts of long chain fatty acids (oleates), sulfonates, animal and vegetable oils (fish oils and castor oil), sulfonated acyclic hydrocarbons, sodium salts of lignin sulfonic acids, alkylnaphthalene sodium sulfonates, sodium lauryl sulfonate, disodium monolauryl phosphate, sorbitol laurate, pentaerythritol monostearate, glyceryl monostearate, poly(oxyethylene), ethylene oxide condensates of stearic acid, stearyl alcohol, stearyl amine, rosin amines, dehydroabietyl amine and the like, lauryl amine salts, dehydroabietyl amine salts, lauryl pyridinium bromide, stearyl trimethylammonium bromide, and cetyl dimethylbenzylammonium chloride. Still other examples are listed in "Detergents and Emulsifiers — 1968 Annual" by John W. McCutcheon.

In addition to the phytotoxic material and application aid material, some specific embodiments of the herbicidal composition of this invention comprise one or more other components, examples of which include other plant growth regulators, insecticides, fungicides, plant nutrients, and the like.

The herbicidal composition of this invention is used by applying it by conventional ways and means to soil and to foliage of weeds.

The rate of application of the composition of this invention is such as to provide an effective concentration of the phytotoxic material in the soil, on the weed foliage, or both in the soil and on the foliage, depending on the method of application and what is desired. In general, satisfactory results are achieved with a phytotoxic material concentration of 1-10 pounds per acre. However, higher and lower concentrations are within the broader concepts of this invention.

A specific embodiment of the dispersible herbicidal composition of this invention, an emulsifiable concentrate, is as follows.

The formulation of this embodiment is:

| Components | Quantities |
|---|---|
| Phytotoxic material | 15 w |
| Acetone | 200 v |
| Emulsifier | 20 v |

The phytotoxic material comprises one or more of the compounds of structural formula I.

The emulsifier recommended for this formulation is a commercially available product identified as Atlox 210 which is a blend of polyoxyethylene (20) sorbitan monooleate with a stabilizing quantity of mono- and diglycerides of fat-forming fatty acids, butylated hydroxyanisole, butylated hydroxytoluene, citric acid and propylene glycol.

In the formulation "w" represents parts by weight, "v" represents parts by volume and "w" is to "v" as the kilogram is to the liter.

The embodiment of the above formulation is made by admixing the components at 20°-25° C.

The concentrate thus formed is used by admixing it with enough water to give an emulsion in which the phytotoxic material is present at the desired concentration. The emulsion is applied by spraying to the soil or to the foliage of weeds.

Typical results in applying the compounds of the use aspect of this invention as well as isomers of these compounds to plants in the greenhouse are presented in the following tables. The compounds were applied singly by spraying an aqueous emulsion of an emulsifiable concentrate of the above formulation. In the pre-emergence tests seeded pots of soil were sprayed uniformly with an amount of the emulsion sufficient to give a coverage of each compound at the rate indicated in Table I, and the pots along with unsprayed seeded pots of soil placed in a greenhouse under favorable germination and growing conditions. When a sufficient amount of time had elapsed for germination of the seeds and growth of the resulting plants had taken place, as evidenced by the unsprayed pots, about 2-3 weeks, the sprayed pots were compared to the unsprayed pots, and the extent of plant injury or kill was determined and graded on a scale from 0 (no kill or injury) to 10 (complete kill). The plants in the pre-emergence tests were:

Water hemp (*Acnida altissima*)
Downy Brome (*Bromus tectorum*)
Giant Foxtail (*Setaria foberii*)
Common Millet (*Setaria species*)
Curled Mustard (*Brassica oleracea*)
Cotton (*Goasypium hirsutum*)
Corn (*Zea Mays*)
Oats (*Avena fatua*)
Lima bean (*Phaseolus limensis*)

The results are set forth in Table I.

TABLE I

Greenhouse Pre-emergence Tests (Soil Germination)

| Compound No. | Name | Rate Lb./acre | Weeds | | | | | | Crops | | | |
|---|---|---|---|---|---|---|---|---|---|---|---|---|
| | | | Water Hemp | Downy Brome | Giant Foxtail | Millet | Curled Mustard | Total Weeds | Cotton | Corn | Oats | Lima Beans |
| 1 | 1-phenyl-3-(2-hexyl)urea | 1 | 6 | 1 | 2 | 2 | 8 | 19 | 1 | 0 | 0 | 0 |
| | | 2 | 9+ | 2 | 6 | 5 | 10 | 32 | 0 | 2 | 3 | 0 |
| | | 4 | 10 | 4 | 7 | 4 | 9+ | 34 | 2 | 2 | 4 | 0 |
| 2 | 1-phenyl-3-(1,2-dimethylbutyl)urea | 1 | 10 | 9 | 9 | 3 | 10 | 41 | 1 | 0 | 3 | 0 |
| | | 2 | 10 | 10 | 10 | 7 | 10 | 47 | 5+ | 2 | 8 | 0 |
| | | 4 | 10 | 10 | 10 | 9 | 10 | 49 | 6 | 3 | 6 | 0 |
| 3 | 1-phenyl-3-(3,3-dimethyl-2-butyl)urea | 1 | 7 | 4 | 5 | 0 | 8 | 24 | 0 | 0 | 0 | 0 |
| | | 2 | 7 | 8+ | 8 | 3 | 10 | 36 | 0 | 2 | 0 | 0 |
| | | 4 | 9+ | 8 | 8+ | 4+ | 10 | 39 | 2 | 5 | 0 | 0 |
| 4 | 1-phenyl-3-(α,α-dimethyl-n-butyl)urea | 1 | 4 | 3 | 4 | 2 | 10 | 23 | 0 | 0 | 0 | 0 |
| | | 2 | 7 | 8 | 7 | 6 | 10 | 38 | 1 | 0 | 0 | 0 |
| | | 4 | 10 | 9 | 8 | 6 | 10 | 43 | 1 | 0 | 0 | 0 |
| 5 | 1-phenyl-3-(2,3-dimethyl-2-butyl)urea | 1 | 8+ | 8 | 10 7+ | 10 7+ | 10 | 40 | | | | |
| | | 2 | 10 | 10 | 9+ | 9+ | 10 | 48 | 3+ | 0 | 2+ | 0 |
| | | 4 | 10 10 | 9+ | 10 | 10 | 49 | 4+ | 3 | 4+ | 0 | |
| 6 | 1-phenyl-3-(1,3-dimethylbutyl)urea | 1 | 8 | 6 | 0 | 0 | 10 | 24 | 0 | 3 | 0 | 0 |
| | | 2 | 7 | 2 | 1 | 1 | 10 | 21 | 0 | 0 | 0 | 0 |
| | | 4 | 10 | 5 | 6 | 4 | 10 | 35 | 1 | 0 | 0 | 0 |
| 7 | 1-phenyl-3-(1-hexyl)urea | 1 | 0 | 0 | 0 | 0 | 0 | 0 | 0 | 0 | 0 | 0 |
| | | 2 | 0 | 0 | 0 | 0 | 0 | 0 | 0 | 0 | 0 | 0 |
| | | 4 | 0 | 0 | 0 | 0 | 0 | 0 | 0 | 2 | 0 | 0 |
| 8 | 1-phenyl-3-(2,2-dimethylbutyl)urea | 1 | 0 | 0 | 0 | 2 | 0 | 2 | 0 | 0 | 0 | 0 |
| | | 2 | 0 | 2 | 2 | 2 | 0 | 6 | 0 | 0 | 0 | 0 |
| | | 4 | 0 | 1 | 2 | 5 | 0 | 8 | 0 | 3 | 0 | |
| 9 | 1-phenyl-3-(3-dimethylbutyl)urea | 1 | 0 | 0 | 0 | 0 | 0 | 0 | 0 | 0 | 0 | 0 |
| | | 2 | 0 | 3 | 6 | 1 | 0 | 10 | 0 | 0 | 0 | 0 |
| | | 4 | 0 | 9+ | 9 | 6 | 0 | 24 | 0 | 5 | 0 | 0 |
| 10 | 1-phenyl-3-(2-ethylbutyl)urea | 1 | 0 | 0 | 0 | 0 | 0 | 0 | 0 | 0 | 0 | 0 |
| | | 2 | 0 | 0 | 0 | 2 | 1 | 3 | 0 | 0 | 0 | 0 |
| | | 4 | 0 | 7 | 4 | 2 | 6+ | 19 | 2 | 0 | 0 | |

The data from Table I on total kill of weeds at the three rates of application are summarized in Table II in which the compounds of Table I are placed in order of toxicity.

TABLE II

Summary of Total Herbicide Activity (Pre-emergence Tests of TABLE I)

| 1 Lb./acre | | 2 Lb./acre | | 4 Lb./acre | |
|---|---|---|---|---|---|
| Compound | Total Weeds | Compound | Total Weeds | Compound | Total Weeds |
| 2 | 41 | 5 | 48 | 2 | 49 |
| 5 | 40 | 2 | 47 | 5 | 49 |
| 3 | 24 | 4 | 38 | 4 | 43 |
| 6 | 24 | 3 | 36 | 3 | 39 |
| 4 | 23 | 1 | 32 | 6 | 35 |
| 1 | 19 | 6 | 21 | 1 | 34 |
| 8 | 2 | 8 | 2 | 9 | 24 |
| 10 | 0 | 10 | 0 | 10 | 19 |
| 9 | 0 | 9 | 0 | 8 | 8 |
| 7 | 0 | 7 | 0 | 7 | 0 |

These data clearly indicate that the Compound 1-6 phenyl hexyl ureas have herbicidal properties distinctly different from the Compound 7-10 phenyl hexyl ureas.

Two of the phenyl hexyl ureas of this invention were field tested in cotton, corn, oats, wheat and sorghum at various rates from 0.5 to 6 pounds per acre. The percent weed control in these crops was determined by comparing with similar, but untreated, plots containing these crops and adjacent the plots with the treated crops. Some plots were treated pre-emergence and post-emergence after the seeded crop had reached the first true leaf stage. The results of the pre-emergence and post-emergence testing of these compounds on cotton, corn and sorghum plots are set forth in Tables III and IV.

TABLE III

| Compound | Field Tests (Pre-emergence) | | | | | | | |
|---|---|---|---|---|---|---|---|---|
| | Rate Lb./acre | % Weed Control | | % Crop Injury | | | | |
| | | Broadleaf | Grasses | Cotton | Corn | Sorghum | Oats | Wheat |
| 1-phenyl-3-(3,3-dimethyl-2-butyl)urea | 1.5 | 75 | 75 | 3 | — | — | — | — |
| | 3.0 | 93 | 97 | 11 | — | — | — | — |
| | 6.0 | 97 | 99 | 51 | — | — | — | — |
| | 1.5 | 88 | 89 | — | 9 | — | 11 | 13 |
| | 3.0 | 95 | 98 | — | 10 | — | 21 | 37 |
| | 6.0 | 98 | 99 | — | 55 | — | 45 | 64 |
| 1-phenyl-3-(2,3-dimethyl-2-butyl)urea | 1.0 | 60 | 52 | — | 0 | — | 0 | 2 |
| | 2.0 | 86 | 89 | — | 0 | — | 18 | 42 |
| | 4.0 | 99 | 98 | — | 42 | — | 70 | 81 |
| | 1.0 | 68 | 13 | 1 | — | — | — | — |
| | 2.0 | 88 | 78 | 9 | — | — | — | — |
| | 4.0 | 97 | 96 | 15 | — | — | — | — |
| | 1.0 | 31 | 21 | — | 0 | 11 | — | — |
| | 2.0 | 45 | 36 | — | 20 | 20 | — | — |
| | 4.0 | 75 | 66 | — | 28 | 32 | — | — |

TABLE IV

| Compound | Field Tests (Post-emergence) | | | | | | |
|---|---|---|---|---|---|---|---|
| | Rate Lb./acre | % Weed Control | | % Crop Injury | | | |
| | | Broadleaf | Grasses | Corn | Sorghum | Oats | Wheat |
| 1-phenyl-3-(3,3-dimethyl-2-butyl)urea | 1.0 | 34 | 26 | 0 | 0 | — | — |
| | 2.0 | 45 | 33 | 3* | 3* | — | — |
| | 4.0 | 62 | 44 | 8* | 4* | — | — |
| | 1.0 | 34 | 30 | 8 | — | 3 | 4 |
| | 2.0 | 53 | 46 | 22 | — | 8 | 8 |
| | 4.0 | 54 | 39 | 15 | — | 3 | 4 |
| 1-phenyl-3-(2,3-dimethyl-2-butyl)urea | 0.5 | 63 | 36 | 8 | — | 8 | 14 |
| | 1.0 | 75 | 45 | 6 | — | 6 | 20 |
| | 2.0 | 63 | 26 | 2 | — | 2 | 22 |
| | 0.5 | 44 | 47 | 0 | 1 | — | — |
| | 1.0 | 57 | 41 | 8 | 18 | — | — |
| | 2.0 | 90 | 75 | 3 | 0 | — | — |

*Roots injured and crop lodging

Thus this invention provides effective ways and means for killing weeds without substantial injury to various crops.

Other features, advantages, and specific embodiments of this invention will become readily apparent to those exercising ordinary skill in the art after reading the foregoing disclosures. In this connection, while specific embodiments of this invention have been described in considerable detail, variations and modifications of these embodiments can be effected without departing from the spirit and scope of the invention as disclosed and claimed.

The expression "consisting essentially of" as used in this specification excludes any unrecited substance at a concentration sufficient to substantially adversely affect the essential properties and characteristics of the composition being defined, while permitting the presence of one or more unrecited substances at concentrations insufficient to substantially adversely affect said essential properties and characteristics.

I claim:

1. A herbicidal composition comprising application aid material and an effective quantity of 1-phenyl-3-(2-hexyl)urea.

2. A herbicidal composition comprising application aid material and an effective quantity of 1-phenyl-3-(1,2-dimethylbutyl)urea.

3. A herbicidal composition comprising application aid material and an effective quantity of 1-phenyl-3-(3,3-dimethyl-2-butyl)urea.

4. A herbicidal composition comprising application aid material and an effective quantity of 1-phenyl-3-(α,α-dimethyl-n-butyl)urea.

5. A herbicidal composition comprising application aid material and an effective quantity of 1-phenyl-3-(1,3-dimethylbutyl)urea.

6. A process for the preemergence control of weeds, which comprises applying to the habitat of said weeds prior to their emergence an effective quantity of at least one compound represented by the structural formula:

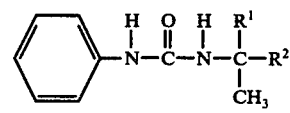

in which $R^1$ is H or $CH_3$, and, when $R^1$ is H, $R^2$ is selected from the group consisting of $CH_2$—$CH_2$—$CH_2$—$CH_3$,

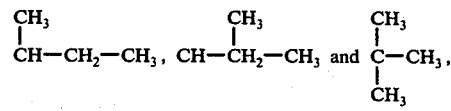

and, when R¹ is CH₃, R² is selected from the group consisting of CH₂—CH₂CH₃ and

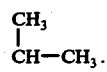

7. A process according to claim 6 in which said compound is 1-phenyl-3-(2-hexyl)urea.

8. A process according to claim 6 in which said compound is 1-phenyl-3-(1,2-dimethylbutyl)urea.

9. A process according to claim 6 in which said compound is 1-phenyl-3-(3,3-dimethyl-2-butyl)urea.

10. A process according to claim 6 in which said compound is 1-phenyl-3-(α,α-dimethyl-n-butyl)urea.

11. A process according to claim 6 in which said compound is 1-phenyl-3-(2,3-dimethyl-2-butyl)urea.

12. A process according to claim 6 in which said compound is 1-phenyl-3-(1,3-dimethylbutyl)urea.

* * * * *